(12) United States Patent
Wang et al.

(10) Patent No.: US 7,313,260 B2
(45) Date of Patent: Dec. 25, 2007

(54) CONTROLLING THICK-SLICE VIEWING OF BREAST ULTRASOUND DATA

(75) Inventors: Shih-Ping Wang, Los Altos, CA (US); Fangyi Rao, San Jose, CA (US)

(73) Assignee: U-Systems, Inc., San Jose, CA (US)

( * ) Notice: Subject to any disclaimer, the term of this patent is extended or adjusted under 35 U.S.C. 154(b) by 0 days.

(21) Appl. No.: 11/489,371

(22) Filed: Jul. 18, 2006

(65) Prior Publication Data

US 2006/0257009 A1     Nov. 16, 2006

Related U.S. Application Data

(63) Continuation of application No. 10/305,661, filed on Nov. 27, 2002, now Pat. No. 7,103,205, which is a continuation-in-part of application No. 10/160,836, filed on May 31, 2002, which is a continuation-in-part of application No. PCT/US01/43237, filed on Nov. 19, 2001.

(60) Provisional application No. 60/415,385, filed on Oct. 1, 2002, provisional application No. 60/326,715, filed on Oct. 3, 2001, provisional application No. 60/252,946, filed on Nov. 24, 2000.

(51) Int. Cl.
*G06K 9/00* (2006.01)

(52) U.S. Cl. ............... 382/128; 600/437; 128/916

(58) Field of Classification Search ........... 382/128, 382/132; 600/437, 443, 447; 128/916; 73/625, 73/626; 378/37

See application file for complete search history.

(56) References Cited

U.S. PATENT DOCUMENTS 3,765,403 A    10/1973   Brenden ............... 128/2 V (Continued)

FOREIGN PATENT DOCUMENTS

EP    0882426 A2    9/1998

(Continued)

OTHER PUBLICATIONS

Bassett, L., "Automated and Hand-Held Breast US: Effect on Patient Management", Radiology 165, pp. 103-108 (1987).

(Continued)

*Primary Examiner*—Andrew W. Johns
(74) *Attorney, Agent, or Firm*—Cooper & Dunham LLP

(57) ABSTRACT

An adjunctive ultrasound mammography system and associated methods are described in which an ultrasound image being displayed near an x-ray mammogram image may be superimposed thereon or thereunder by a user for facilitating rapid comprehension of breast structures and detection of abnormalities therein. In one preferred embodiment, the x-ray mammogram image corresponds to a standard x-ray mammogram view, and the ultrasound image is a thick-slice image representing a thick-slice or slab-like portion of the breast volume substantially parallel to that standard x-ray mammogram view. In another preferred embodiment, the user is permitted to manually manipulate the registration of the ultrasound image with the x-ray mammogram image. It has been found that the manual registration process, which involves manual vernier adjustments responsive to perceived registration differences, can rapidly increase the radiologist's perception of the breast structures being displayed by both component images. Even though ultrasound images tend to have substantially different textures and feature emphases than x-ray images, the bimodal thick-slice/x-ray image, alone or in conjunction with the vernier registration process, can often expose or clarify tissue structures hidden in the separate component images, and can often obviate or explain certain noticed structures in the component images.

20 Claims, 12 Drawing Sheets

U.S. PATENT DOCUMENTS

| | | | |
|---|---|---|---|
| 4,167,180 A | 9/1979 | Kossoff | 128/660 |
| 4,282,880 A | 8/1981 | Gardineer et al. | 128/660 |
| 4,298,009 A | 11/1981 | Mezrich et al. | 128/660 |
| 4,485,819 A | 12/1984 | Igl | 128/660 |
| 4,722,345 A | 2/1988 | Ueno et al. | 128/660 |
| 4,729,019 A | 3/1988 | Rouvrais | 358/112 |
| 4,796,632 A | 1/1989 | Boyd et al. | 128/662.03 |
| 4,930,143 A | 5/1990 | Lundgren et al. | 378/37 |
| 5,078,142 A | 1/1992 | Siczek et al. | 128/653.1 |
| 5,079,698 A | 1/1992 | Grenier et al. | 364/413.13 |
| 5,133,020 A | 7/1992 | Giger et al. | 382/6 |
| 5,379,769 A | 1/1995 | Ito et al. | 128/660.07 |
| 5,396,890 A | 3/1995 | Weng | 128/660.07 |
| 5,433,202 A | 7/1995 | Mitchell et al. | 128/660.08 |
| 5,488,952 A | 2/1996 | Schoolman | 178/660.07 |
| 5,491,627 A | 2/1996 | Zhang et al. | 364/413.2 |
| 5,503,152 A | 4/1996 | Oakley et al. | 128/661.01 |
| 5,511,026 A | 4/1996 | Cleveland et al. | 365/189.09 |
| 5,603,326 A | 2/1997 | Richter | 128/660.07 |
| 5,640,956 A | 6/1997 | Getzinger et al. | 128/653.1 |
| 5,660,185 A | 8/1997 | Schmulewitz et al. | 128/749 |
| 5,662,109 A | 9/1997 | Hutson | 128/653.1 |
| 5,664,573 A | 9/1997 | Schmulewitz | 128/660.09 |
| 5,671,294 A | 9/1997 | Rogers et al. | 382/228 |
| 5,673,332 A | 9/1997 | Nishikawa et al. | 382/128 |
| 5,709,206 A | 1/1998 | Teboul | 128/653.1 |
| 5,729,620 A | 3/1998 | Wang | 382/128 |
| 5,734,384 A | 3/1998 | Yanof et al. | 345/424 |
| 5,776,062 A | 7/1998 | Nields | 600/407 |
| 5,779,641 A | 7/1998 | Hatfield et al. | 600/443 |
| 5,790,690 A | 8/1998 | Doi et al. | 382/128 |
| 5,803,082 A | 9/1998 | Stapleton et al. | 128/653.1 |
| 5,815,591 A | 9/1998 | Roehrig et al. | 382/130 |
| 5,820,552 A | 10/1998 | Crosby et al. | 600/407 |
| 5,828,774 A | 10/1998 | Wang | 382/128 |
| 5,833,627 A | 11/1998 | Shmulewitz et al. | 600/562 |
| 5,840,032 A | 11/1998 | Hatfield et al. | 600/443 |
| 5,851,180 A | 12/1998 | Crosby et al. | 600/407 |
| 5,865,750 A | 2/1999 | Hatfield et al. | 600/443 |
| 5,899,863 A | 5/1999 | Hatfield et al. | 600/443 |
| 5,904,653 A | 5/1999 | Hatfield et al. | 600/454 |
| 5,917,929 A | 6/1999 | Marshall et al. | 382/128 |
| 5,919,139 A | 7/1999 | Lin | 600/443 |
| 5,934,288 A | 8/1999 | Avila et al. | 128/916 |
| 5,935,071 A | 8/1999 | Schneider et al. | 600/445 |
| 5,938,613 A | 8/1999 | Shmulewitz et al. | 600/461 |
| 5,954,650 A | 9/1999 | Saito et al. | 600/425 |
| 5,964,707 A | 10/1999 | Fenster et al. | 600/443 |
| 5,983,123 A | 11/1999 | Shmulewitz | 600/407 |
| 5,984,870 A | 11/1999 | Giger et al. | 600/443 |
| 5,997,477 A | 12/1999 | Sehgal | 600/437 |
| 6,027,457 A | 2/2000 | Shmulewitz et al. | 600/562 |
| 6,035,056 A | 3/2000 | Karssemeijer | 382/128 |
| 6,068,597 A | 5/2000 | Lin | 600/443 |
| 6,075,879 A | 6/2000 | Roehrig et al. | 382/132 |
| 6,091,841 A | 7/2000 | Rogers et al. | 382/132 |
| 6,102,861 A | 8/2000 | Avila et al. | 600/443 |
| 6,102,866 A | 8/2000 | Nields et al. | 600/461 |
| 6,117,080 A | 9/2000 | Schwartz | 600/443 |
| 6,155,978 A | 12/2000 | Cline et al. | 600/443 |
| 6,157,697 A | 12/2000 | Mertelmeier et al. | 378/37 |
| 6,181,769 B1 | 1/2001 | Hoheisel et al. | 378/98.8 |
| 6,190,334 B1 | 2/2001 | Lasky et al. | 600/587 |
| 6,198,838 B1 | 3/2001 | Roehrig et al. | 382/132 |
| 6,254,538 B1 | 7/2001 | Downey et al. | 600/439 |
| 6,263,092 B1 | 7/2001 | Roehrig et al. | 382/128 |
| 6,266,435 B1 | 7/2001 | Wang | 382/132 |
| 6,269,565 B1 | 8/2001 | Inbar et al. | 40/361 |
| 6,278,793 B1 | 8/2001 | Gur et al. | 382/128 |
| 6,282,305 B1 | 8/2001 | Huo et al. | 382/128 |
| 6,301,378 B1 | 10/2001 | Karssemeijer et al. | 382/132 |
| 6,311,419 B1 | 11/2001 | Inbar | 40/361 |
| 6,317,617 B1 | 11/2001 | Gilhuijs et al. | 600/408 |
| 6,377,838 B1 | 4/2002 | Iwanczyk et al. | 600/425 |
| 6,385,474 B1 | 5/2002 | Rather et al. | 600/407 |
| 6,413,219 B1 | 7/2002 | Avila et al. | 600/443 |
| 6,450,962 B1 | 9/2002 | Brandl et al. | 600/458 |
| 6,459,925 B1 | 10/2002 | Nields et al. | 600/427 |
| 6,628,815 B2 | 9/2003 | Wang | 382/132 |
| 6,630,937 B2 | 10/2003 | Kallergi et al. | 345/619 |
| 6,682,484 B1 | 1/2004 | Entrekin et al. | 600/437 |
| 2002/0113683 A1 | 8/2002 | Yu | 337/126 |
| 2002/0145941 A1* | 10/2002 | Poland et al. | 367/11 |
| 2002/0173722 A1 | 11/2002 | Hoctor et al. | 600/443 |
| 2003/0181801 A1 | 9/2003 | Lasser et al. | 600/407 |
| 2004/0015080 A1 | 1/2004 | Kelly et al. | 600/437 |

FOREIGN PATENT DOCUMENTS

| | | |
|---|---|---|
| EP | 0730431 B1 | 3/2000 |
| WO | WO94/21189 A2 | 9/1994 |
| WO | WO02/17792 A1 | 3/2002 |
| WO | WO2004/064644 A1 | 8/2004 |

OTHER PUBLICATIONS

Buchberger, W., et al., "Incidental Findings on Sonography of the Breast: Clinical Significance And Diagnostic Workup", American Journal of Radiology (AJR) 173, pp. 921-927 October 1999.

Carson, P. et al., "Lesion Detectability in Ultrasonic Computed Tomography of Symptomatic Breast Patients", Investigative Radiology, vol. 23, No. 6, pp. 421-427, Jun. 1998.

Chen et al., "Computer-aided Diagnosis Applied to US of Solid Breast Nodules by Using Neural Networks", Radiology, pp. 407-412, Nov. 1999.

Cheng et al., "Automated Detection of Breast Tumors in Ultrasonic Images Using Fuzzy Reasoning", Proceedings of the IEEE Computer Society International Conference on Image Processing vol. III, pp. 420-423, Oct. 26-29, 1997.

Dawant, Benoit M. et al., "Image Segmentation", Handbook of Medical Imaging, vol. 2; Medical Image Processing and Analysis, Sonka and Fitzpatrick, eds., Chapter 2, pp. 98-101, SPIE Press (2000).

Giger et al., "Computer-Aided Diagnosis in Mammography", Handbook of Medical Imaging, vol. 2: Medical Image Processing and Analysis, Sonka and Fitzpatrick, Chapter 15, pp. 915-1004, SPIE Press 2000.

Heywang-Kobrunner, Dershaw and Schreer, Diagnostic Breast Imaging, pp. 87-102, Thieme Publishers 2001.

Jackson, Valerie P., "Controversies in Ultrasound Screening", Society of Breast Imaging 5th Postgraduate Course, May 16-19, 2001, Sheraton Harbor Island, San Diego, CA, pp. 93-95 May 16, 2001.

Jalali, "Sound Combination: Ultrasound Paired With Mammography Can Improve Cancer Detection for Dense-Breasted Woman", ADVANCE for Administrators In Radiology and Radiation Oncology, pp. 68-70, Mar. 1999.

Kopans, D. et al., "Whole-Breast US Imaging: Four Year Follow-Up", Radiology 157: 505-507 1985.

Kopans, "Breast Cancer Screening With Ultrasonography", Lancet, vol. 354, pp. 2096-2097, Dec. 18/25, 1999).

Labsonics, Inc., "Labsonics Ultrasound Breast Scanner: Accurate, High-Performance Investigation of the Breast for Confident Diagnosis", 8-page product brochure from Labsonics, Inc., Mooresville, Indiana, 1983.

Lehman et al., "Effect of Age and Breast Density on Screening Mammograms with False-Positive Findings", American Journal of Radiology (AJR) 173: 1651-1655, Dec. 1999.

LORAD, a Hologic Company, "Fully Automatic Self-Adjusting Tilt Compression Plate", 3 page product description downloaded and printed on May 22, 2002 from www.loradmedical.com/p225.html.

Lowers, J., "Experimental Modes Abound for Detecting Breast Cancer: Vibrational Resonance Technique Among the Contenders", Women's Health Supplement to Diagnostic Imaging, pp. 15-17, Apr. 2001.

McKnoulty, L., "Ultrasound has Unique Strengths In Breast Imaging", 3-page printout from www.auntminnie.com one Mar. 1, 2002, Jan. 2002.

Mendelson, Ellen B., "Current Status of Breast US", RSNA Categorical Course In Breast Imaging, pp. 295-309, 1999.

Qayyum, A. et al., "MR Imaging Features of Infiltrating Lobular Carcinoma of the Breast: Histopathologic Correlation", American Journal of Radiology (AJR) 178: 1227-1232, May 2002.

Rahbar, G. et al., "Benign Versus Malignant Solid Breast Masses: US Differentiation", Radiology 213:889-894, 1999.

Rapp, Cynthia L., "Breast Ultrasound", Lecture Notes for EDA AHP 230-0406, Health & Sciences Television Network, Primedia Healthcare, Carrolton TX, Mar. 2000.

Richter, K. et al., "Quantitative Parameters Measured by a New Sonographic Method for Differentiation of Benign and Malignant Breast Disease", Investigative Radiology, vol. 30, No. 7, pp. 401-411, Jul. 1995.

Richter, K. et al., "Detection of Diffuse Breast Cancers with a New Sonographic Method", J. Clinical Ultrasound 24: pp. 157-168, May 1996.

Richter, K. et al., "Differentiation of Breast Lesions by Measurements Under Craniocaudal and Lateromedial Compression Using a New Sonographic Method", Investigative Radiology, vol. 31, No. 7, pp. 401-414, Jul. 1996.

Richter, K. et al., "Description and First Clinical Use of a New System for Combined Mammography and Automated Clinical Amplitude/Velocity Reconstructive Imaging Breast Sonography", Investigative Radiology, vol. 32, No. 1, pp. 19-28, Jan. 1997.

Richter, K. et al., "Detection of Malignant and Benign Breast Lesions with an Automated US US System: Results in 120 Cases", Radiology 205: pp. 823-830, Dec. 1997.

Russ, "The Image Processing Handbook, 3$^{rd}$ Edition", CRC Press/ IEEE Press, p. 264, 1998.

Schreiman, J. et al., "Ultrasound Transmission Computed Tomography of the Breast", Radiology 150; pp. 523-530, 1984.

Singh, S. and Al-Mansoori, R., "Identification of Regions of Interest in Digital Mammograms", J. Intelligent Systems10:2, 2000.

Smith, D., "Breast Ultrasound", Radiologic Clinics of North America, vol. 39, No. 3, pp. 485-497, May 2001.

"Ultrasound RSNA Preview: Productivity and Ease of Use Dominate New Ultrasound Productss", Medical Imaging, pp. 55-56, Nov. 1999.

Zonderland, H. et al., "Diagnosis of Breast Cancer: Contribution of US as an Adjunct of Mammography", Radiology 213: 413-422, 1999.

Dec. 28, 2005 International Search Report and Written Opinion in Connection with International Application PCT/US05/19604.

\* cited by examiner

CONTROLLING THICK-SLICE VIEWING OF BREAST ULTRASOUND DATA

CROSS-REFERENCE TO RELATED APPLICATIONS

This application is a continuation of U.S. Ser. No. 10/305,661, filed Nov. 27, 2002, now U.S. Pat. No. 7,103,205, which is a continuation-in-part of U.S. Ser. No. 10/160,836, filed May 31, 2002, which is a continuation-in-part of International Application Ser. No. PCT/US01/43237, filed Nov. 19, 2001. Ser. No. PCT/US01/43237 claims the benefit of U.S. Provisional Ser. No. 60/252,946, filed Nov. 24, 2000. Ser. No. 10/160,836 also claims the benefit of U.S. Provisional Ser. No. 60/326,715, filed Oct. 3, 2001. Ser. No. 10/305,661 also claims the benefit of Provisional Application No. 60/415,385, filed Oct. 1, 2002. Each of the above-mentioned applications is incorporated by reference herein. The subject matter of the present application is related to the subject matter of Ser. No. 10/305,936 filed Nov. 27, 2002, which is incorporated by reference herein.

FIELD

This patent specification relates to medical imaging systems and processes. In particular, the present invention relates to the acquisition and display of breast ultrasound information in a manner that facilitates breast cancer screening.

BACKGROUND

Breast cancer is the most common cancer among women other than skin cancer, and is the second leading cause of cancer death in women after lung cancer. The American Cancer Society currently estimates that there are about 203,500 new invasive cases of breast cancer per year among women in the United States and 39,600 deaths per year from the disease. Prevention and early diagnosis of breast cancer are of foremost importance. Because early breast cancer does not produce symptoms, the American Cancer Society recommends a screening mammogram and a clinical breast examination every year for women over the age of 40.

X-ray mammography is currently the only imaging method for mass screening of breast cancer. In health maintenance organizations (HMOs) and other medical organizations, specialized x-ray mammography clinics designed for high patient throughput are being increasingly used to screen as many women as possible in a time and cost efficient manner. Numerous studies have shown that early detection saves lives and increases treatment options. Recent declines in breast cancer mortality rates (e.g., 39,600 deaths in 2002 versus 41,200 in 2000) have been attributed, in large part, to the regular use of screening x-ray mammography.

It has been found that the use of ultrasound mammography (sonomammography) in conjunction with conventional x-ray mammography can drastically increase the early breast cancer detection rate. Whereas x-ray mammograms only detect a summation of the x-ray opacity of individual slices over the entire breast, ultrasound can separately detect the acoustic impedance of individual slices of breast tissue, and therefore may allow detection of breast lesions where x-ray mammography alone fails.

However, as discussed in Ser. No. 10/160,836, supra, despite strong evidence that use of independent ultrasound examination would improve early breast cancer detection and therefore save lives, substantial resistance against such use currently exists in the medical industry, including the radiologists themselves, and among policymakers. As used herein, the term "radiologist" generically refers to a medical professional that analyzes medical images and makes clinical determinations therefrom, it being understood that such person might be titled differently, or might have differing qualifications, depending on the country or locality of their particular medical environment. Several interrelated factors are often cited, including: (i) the false negative (missing) rate of independent ultrasound examination is unknown, (ii) the false positive rate of independent ultrasound examination is known to be very high, leading to an increase in unneeded patient callbacks and biopsies, (iii) lack of image acquisition standardization, leading to variability among different operators and radiologists, (iv) the additional time and equipment required to conduct the ultrasound examination, leading to an increase in cost, (v) most if not all radiologists are not trained to read screening ultrasound images, which contain features not found in current breast imaging textbooks or taught in current medical school courses, leading to a potential increase in false negative (missing) rate and in the additional radiologist time required to analyze the ultrasound images, and (vi) the additional training and clinical experience that would be required for the radiologist to properly analyze the ultrasound images.

Various schemes have been proposed for processing and presenting breast ultrasound information in conjunction with x-ray mammogram information for use in breast cancer detection environments. In U.S. Pat. No. 5,938,613, which is incorporated by reference herein, a method and apparatus for performing sonomammography and enhanced x-ray imaging is discussed in which ultrasound equipment is integrated with mammography equipment to generate ultrasonic images of the breast that are in geometric registration with an x-ray mammogram. An x-ray mammogram image of an immobilized breast is acquired and, while the breast is still immobilized, an ultrasound scan is acquired using an automated ultrasound probe translation mechanism. Cross-sectional ultrasonic slices are summed across the entire breast to form a two-dimensional ultrasound image, which is then overlaid onto the digitized x-ray image for viewing by the radiologist. Precise geometric registration between the ultrasound image and the x-ray mammogram is automatically provided because the breast is immobilized between imaging procedures and because the coordinates of the ultrasound probe are known during each scan. The radiologist is permitted to instantiate certain algorithms such as digital subtraction between the registered medical images.

However, the '613 patent is deficient in several respects with respect to the practical, real-world factors associated with the current resistance against the use of ultrasound in mass breast cancer screening environments. For example, the large base of currently installed x-ray imaging systems would require substantial retooling to accommodate the mechanical apparatus of the '613 patent that keeps the breast immobilized between imaging procedures and that performs the automated ultrasound scans. As another example, by displaying a summation ultrasound image of all breast slices together, the '613 method deprives the radiologist of the ability to view individual planes inside the breast. More generally, the computer-registered, static overlay of the summation ultrasound image onto the x-ray image affords only a limited amount of ultrasonic information to the radiologist as compared to the actual amount of ultrasonic data actually acquired, and affords only limited perception by the radiologist of structures within the breast.

In U.S. Pat. No. 5,662,109, a method and system for multi-dimensional imaging and analysis for early detection of diseased tissue is discussed. Ultrasound scans of a breast are processed into multiple layers of two-dimensional images, thus yielding a three-dimensional data set. This data set and a two-dimensional x-ray mammogram are input to an enhancer that performs one or more "data fusion" algorithms to generate a three-dimensional representation of the breast for viewing. The enhancer includes a registration module that expands and/or reduces dimensions of the data to register and align the ultrasound and mammographic images.

However, it is not believed that the various three-dimensional views of the "fused" data discussed in the '109 patent, such as the perspective view shown in FIG. 1 thereof, would be useful to a typical radiologist trained in conventional x-ray mammography methods. As described supra, radiologists typically spend many years developing expertise in analyzing a very particular set of two-dimensional x-ray mammographic data taken from standardized views, most commonly the craniocaudal (CC) and mediolateral oblique (MLO) views. It is believed that most radiologists would be reluctant to "start over again" with an entirely new, different way of viewing the complex structures of a breast, and that the medical industry would likewise be reluctant to force radiologists to accept these viewing methods.

In view of the above discussions, it would be desirable to provide an adjunctive ultrasound mammography system that integrates ultrasound mammography into current breast cancer screening methodologies.

It would be further desirable to provide an adjunctive ultrasound mammography system that displays breast ultrasound information in a manner that facilitates the radiologist's perception of internal breast structures that may not be readily apparent in an x-ray mammogram, while also being able to confirm the radiologist's perception of internal breast structures that are apparent in the x-ray mammogram.

It would be even further desirable to provide an adjunctive ultrasound mammography system that displays breast ultrasound information in a manner that supplements, rather than replaces, conventional x-ray mammogram viewing methods, thereby increasing the likelihood of adoption by both individual radiologists and the medical industry.

It would be even further desirable to provide an adjunctive ultrasound mammography system that takes little or no special familiarization or training from the radiologist in order to effectively view breast ultrasound information.

SUMMARY

An adjunctive ultrasound mammography system and associated methods are provided including an adjunctive ultrasound display system configured to allow flexible, intuitive, and interactive viewing of breast ultrasound information in a manner that complements x-ray mammogram viewing. An ultrasound image of a breast is displayed near an x-ray mammogram image of the breast, the adjunctive ultrasound display system allowing for superposition of the ultrasound image over the x-ray mammogram image, or vice-versa, for facilitating rapid comprehension of breast structures and detection of abnormalities therein. In one preferred embodiment, the x-ray mammogram image corresponds to a standard x-ray mammogram view, and the ultrasound image is a thick-slice image representing a thick-slice or slab-like portion of the breast volume substantially parallel to that standard x-ray mammogram view. In another preferred embodiment, the user is permitted to perform manual vernier adjustments of the registration of the ultrasound image with the x-ray mammogram image.

Advantageously, thick-slice ultrasound images corresponding to standard x-ray mammogram view planes are of immediate and familiar significance to the radiologist, both as stand-alone images and as components of bimodal ultrasound/x-ray images. Moreover, it has been found that the manual vernier registration adjustment process itself, in which the radiologist shifts the relative positions of the component images responsive to perceived registration differences, can rapidly increase the radiologist's perception and appreciation of the breast structures being displayed by both component images. Even though ultrasound images tend to have substantially different textures and feature emphases than x-ray images, the resulting bimodal image, alone or in combination with the manual vernier registration adjustment process, can often expose or clarify tissue structures that may be hidden or less apparent in the separate x-ray mammogram and/or ultrasound images, and can often obviate or explain certain noticed structures in the separate x-ray mammogram and/or ultrasound images.

Preferably, an array of thick-slice images is displayed to the radiologist representing different thick-slice portions of the breast, and the radiologist can manually superimpose any one of them over the x-ray mammogram image, or can manually superimpose the x-ray mammogram image over any one of them. In one preferred embodiment, both the x-ray mammogram image and the ultrasound image are displayed on the same screen of a high-resolution monitor, and a pixelwise digital mixing algorithm is used to achieve image superposition. Preferably, a mixing algorithm is selected that approximates the visual effect of (i) placing a conventional x-ray mammogram film on a light box, and (ii) superimposing a second transparency thereon containing a printed version of the thick-slice ultrasound image. However, the incorporation of any of a variety of digital mixing algorithms is within the scope of the preferred embodiments, including those that permit dynamic adjustment of one or more mixing parameters by the radiologist, and including both pixelwise and neighborhood-based mixing algorithms.

In other preferred embodiments, the component medical images are presented in any of a variety of physical configurations that permit the user to overlay them to form a bimodal image and to perform fine registration adjustments. The component medical images may exist on x-ray film, as lightbox backprojections, on high-brightness computer monitors, on transparent or opaque hardcopies, on subtractive liquid crystal displays, and/or on other types of image displays, and in different combinations thereof, provided that image superposition is possible. Any of a variety of mechanisms may be used to physically move/overlay the medical images and to provide manual vernier adjustment capability, ranging from hand manipulation of hardcopy images to computerized click-and-drag techniques.

In one preferred embodiment in which the ultrasound image is displayed in electronic format, user inputs are provided for allowing dynamic adjustment of (i) the thickness of the thick-slice image, i.e., the thickness of the slab-like region of the breast that is integrated into a single two-dimensional thick-slice image, and (ii) thick-slice image elevation, i.e., the vertical elevation of the slab-like region within the breast volume. In one preferred embodiment, the positioning of the overlying image onto the underlying image is an entirely manual process, the radiologist manually performing both (i) preliminary or coarse registration, i.e., moving the images from their initial positions onto each other, and (ii) vernier registration, i.e., perfecting the registration of the images. In an alternative preferred embodiment, preliminary registration is provided automatically by the display system using any of a variety of known methods, such that the radiologist only needs to perform the vernier registration step.

Preferably, in an adjunctive ultrasound system using ultrasound overlays according to a preferred embodiment, the ultrasound image information is provided to the radiologist on a supplementary, as-needed basis, without interfering with the radiologist's primary task of analyzing x-ray mammograms. This is believed to be advantageous from a strategic medical-community acceptance viewpoint, because entrenched radiologists will not be "forced" to use the ultrasound information. Once called upon, however, it is expected that the convenient, easy-to-use, intuitive ultrasound information viewing system according to the preferred embodiments will attract many radiologists to its use in everyday mass breast cancer screening activities.

DETAILED DESCRIPTION

Figure 1:
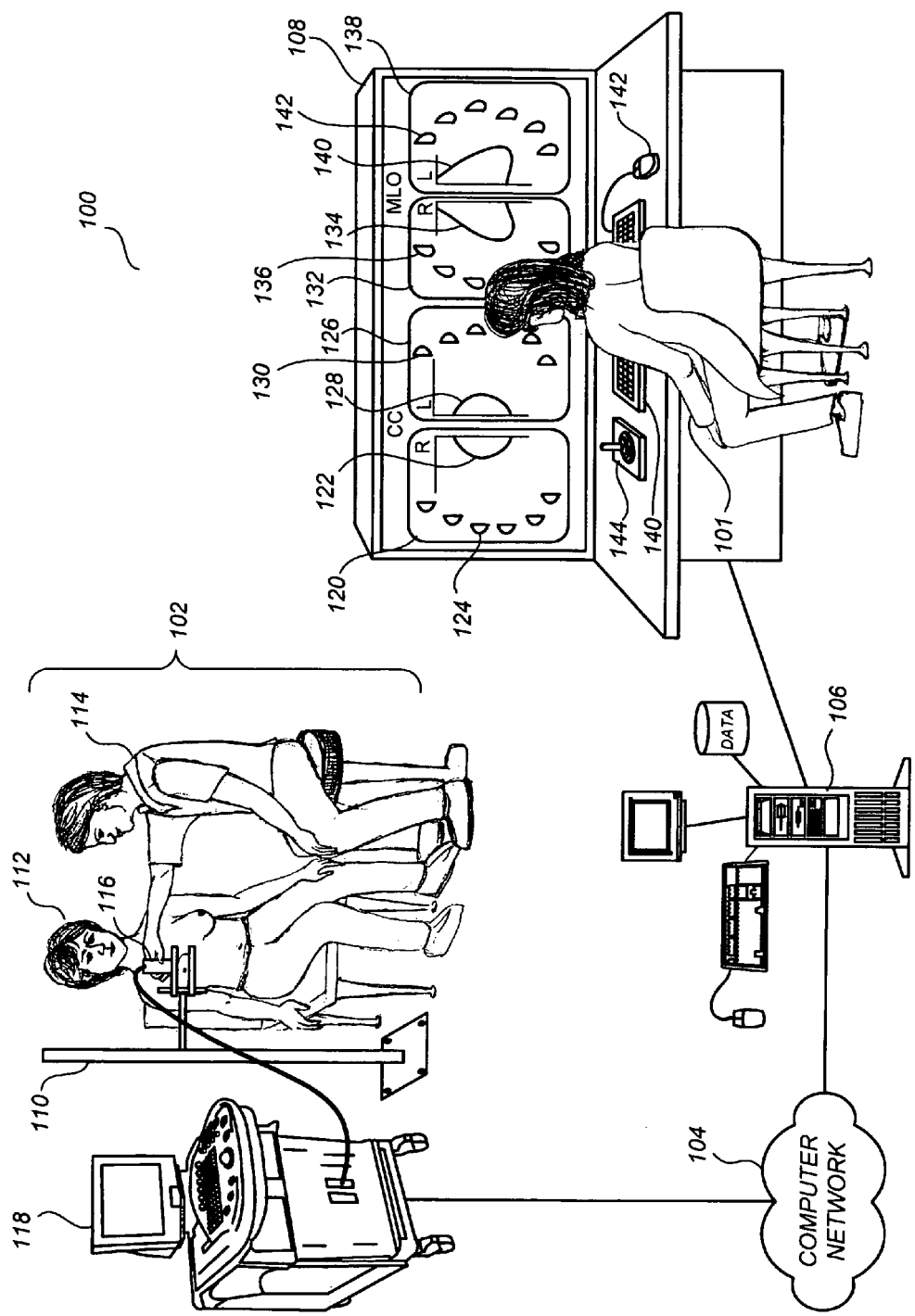
FIG. 1 illustrates a conceptual diagram of a system and method for breast cancer screening using adjunctive ultrasound mammography according to a preferred embodiment.

FIG. 1 illustrates a conceptual diagram of a system 100 and associated methods for breast cancer screening using adjunctive ultrasound mammography according to a preferred embodiment. Many aspects of the system 100 are also described in Ser. No. 10/160,836, supra. Adjunctive ultrasound mammography refers to the acquisition and display of breast ultrasound information during the breast cancer screening process in a manner that supplements x-ray mammogram information. System 100 comprises an ultrasound scanning station 102, a computer network 104, an adjunctive ultrasound server 106, and an adjunctive ultrasound screening station 108. Ultrasound scanning station 102 comprises an ultrasound scanning apparatus 110 for facilitating breast ultrasound scans of the patient 112 by an ultrasound technician 114. An ultrasound probe 116 is used to scan a breast of the patient 112, with reflected acoustic interrogation signals being processed by an ultrasound machine 118.

Preferable to the ultrasound scanning station 102 of FIG. 1 are ultrasound scanning unit described more fully in Ser. Nos. 60/415,385 and 10/160,836, supra.

The ultrasound scanning apparatus 110 supports and maintains the breast during the ultrasound scanning process. According to a preferred embodiment, the ultrasound scanning apparatus 110 also flattens the breast along a plane parallel to a standard x-ray mammogram view plane such that resulting ultrasound images correspond more closely to standard x-ray mammogram images. In the example of FIG. 1, the standard x-ray mammogram view is the craniocaudal (CC) view. While described herein with respect to the CC view for simplicity and clarity of explanation, it is to be appreciated that the preferred embodiments are readily applied to the mediolateral oblique (MLO) view or to standard or custom x-ray mammogram views.

Although not shown in FIG. 1, the patient 112 also undergoes a standard x-ray mammography procedure in addition to the ultrasound mammography procedure. The x-ray mammogram is usually taken during the same office visit as the ultrasonic mammography scans, although the scope of the preferred embodiments is not so limited. The ultrasound technician 114 may be the same person or a different person as the x-ray technician who performs the x-ray mammography procedure.

If the ultrasound probe 116 is manipulated by hand, as in the embodiment of FIG. 1, a position sensing system (not shown) is used to track the probe position such that the acquired ultrasound frames may be processed into a three-dimensional volumetric representation of the breast. It is generally preferable, however, that the ultrasound probe 116 be machine-manipulated and controlled so as to provide reliable, consistent ultrasound scans. The ultrasound scans should be of sufficient resolution and taken at small enough intervals such that the three-dimensional volumetric representation has sufficient resolution to enable computer-aided diagnosis (CAD) algorithms to perform effectively, and such that both individual ultrasound slices and thick-slice images are of sufficient resolution to enable meaningful screening assistance to the radiologist.

As will be described further infra, the raw ultrasound scans may be taken directly in the standard x-ray mammogram view plane, or may alternatively be taken from a different orientation. When the raw ultrasound scans are taken directly in the standard x-ray mammogram view plane, each individual ultrasound slice is computed directly from an acquired two-dimensional ultrasound image or ultrasound frame. When the raw ultrasound scans are taken from a different orientation, each individual ultrasound slice corresponds to a plane of voxels (volume elements) in a three-dimensional volumetric representation of the breast, the plane of voxels being oriented in a direction parallel to the standard x-ray mammogram view plane. Most commonly, the three-dimensional volumetric representation of the breast is computed from the raw ultrasound scans, and then the individual ultrasound slice is extracted therefrom. However, in other preferred embodiments such as those described in Ser. No. 60/326,715, supra, it is not always necessary to reconstruct the entire three-dimensional volumetric representation to compute the individual ultrasound slices. Stated more generally, if the raw ultrasound scans are taken in planes directly parallel to a plane of interest (CC, MLO, or a different "custom" plane of importance), each individual ultrasound slice is computed directly from an acquired two-dimensional ultrasound image or ultrasound frame, whereas if the raw ultrasound scans are taken from directions different than the plane of interest, each individual ultrasound slice corresponds to a plane of voxels in a three-dimensional volumetric representation of the breast in a direction parallel to the plane of interest.

Ultrasound machine 118 may generally comprise any commercially available ultrasound machine having sufficient resolution, speed, and network connectivity to achieve the functionalities described herein. During or after the ultrasound scanning process, the raw ultrasound data is provided across the computer network 104 to the adjunctive ultrasound server 106, where the raw ultrasound data is processed into adjunctive ultrasound data that will be made available to the screening radiologist, the adjunctive ultrasound data including ultrasound slices, thick-slice images, vibrational Doppler imaging (VDI) images, CAD outputs, and other useful information. It is to be appreciated that the processing of the raw ultrasound data into the adjunctive ultrasound data may be performed by any of a variety of different computing devices coupled to the computer network 104 and then transferred to the adjunctive ultrasound server 106.

Although many different variations are within the scope of the preferred embodiments, in the example of FIG. 1 the adjunctive ultrasound screening station 108 comprises four display monitors, each dedicated to a particular standard x-ray mammogram view for each breast. On a first display monitor 120, a right CC x-ray mammogram image 122 is displayed, with a plurality of ultrasound thick-slice thumbnail images 124 being distributed in an arc-like pattern therearound as shown in FIG. 1. The thumbnail thick-slice images 130 represent thick-slice portions of the left breast volume oriented parallel to the CC view plane. A second display monitor 126 displays a left CC x-ray view 128 and associated ultrasound thick-slice thumbnails 130, a third display monitor 132 displays a right MLO x-ray view 134 and associated ultrasound thick-slice thumbnails 136, and a fourth display monitor 138 displays a left MLO x-ray view 140 and associated ultrasound thick-slice thumbnails 142. For simplicity and clarity of explanation, only the left CC view monitor 126 is detailed herein, it being understood that similar descriptions apply to the other standard x-ray mammogram views.

Generally speaking, a thick-slice image is an integration of a plurality of substantially parallel individual ultrasound slices used to represent a slab-like or thick-slice volume of the breast. The thickness of the slab-like or thick-slice volume may lie, for example, in the range of 2 mm to 20 mm, although the scope of the preferred embodiments is not so limited. Techniques for integrating the component ultrasound slices into thick-slice images according to the preferred embodiments include arithmetic averaging, geometric averaging, reciprocal averaging, exponential averaging, and other averaging methods, in each case including both weighted and unweighted averaging techniques. Other suitable integration methods may be based on statistical properties of the population of component ultrasound slices at common locations, such as maximum value, minimum value, mean, variance, or other statistical algorithms. Generally speaking, the ultrasound thick-slice images and thumbnails described herein are similar to those described in Ser. No. 10/160,836, supra.

In the preferred embodiment of FIG. 1, at the outset of the display process, the ultrasound thick-slice thumbnails 130 are of sufficient number and thickness to represent the entire breast volume. For example, if the compressed breast volume has a total elevation of 6 cm, there can be six individual thick-slice thumbnails each corresponding to 1 cm slab-like regions within the breast. The x-ray mammogram image 128 is preferably displayed at full-scale. If the display monitor 126 is sufficiently large, the thick-slice thumbnails can be replaced with full-scale thick-slice images if desired.

Adjunctive ultrasound screening station 108A further comprises a control panel positioned near or integrated with each display monitor 120, 126, 132, and 138. In the simple example of FIG. 1 a keyboard 140, a mouse 142, and a joystick 144 are provided through which user control and the manual image manipulations infra are achieved. It is to be appreciated that the user controls and manual image manipulations described herein are in addition to the user controls and other features described in Ser. No. 10/160,836, supra.

Figure 4:
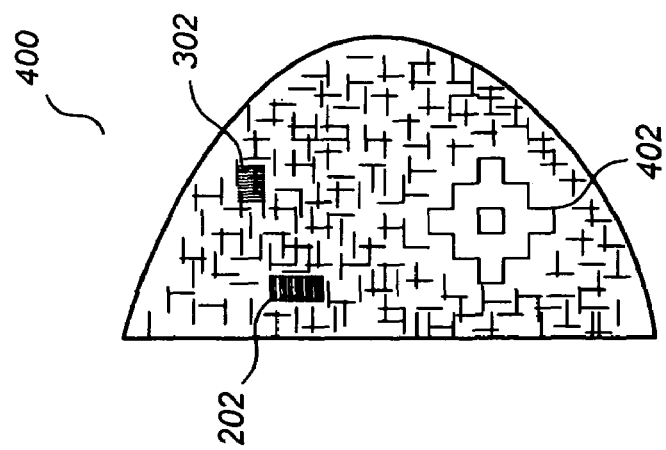
FIG. 4 illustrates a conceptual diagram of a bimodal medical image formed from the medical images of FIGS. 2 and 3.
Figure 3:
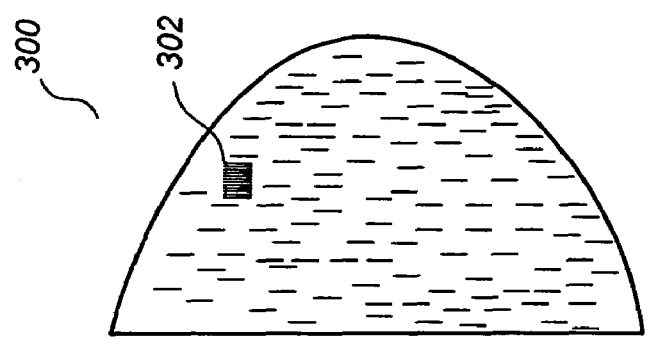
FIG. 3 illustrates a conceptual diagram of a second medical image of a breast.
Figure 2:
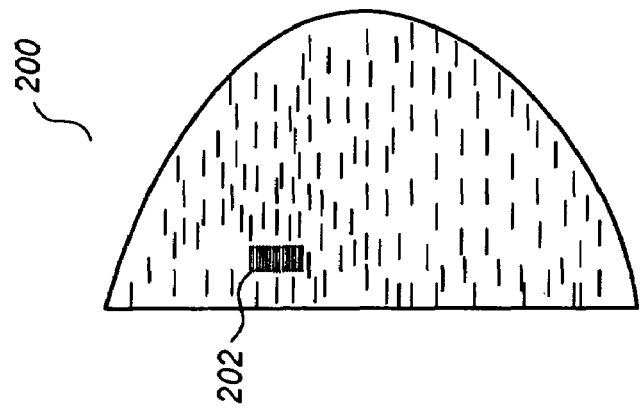
FIG. 2 illustrates a conceptual diagram of a first medical image of a breast.

FIGS. 2-4 are conceptual diagrams intended to communicate, in a simplified hypothetical setting, the analytical assistance that an overlay of two medical images of two different modalities can provide. FIG. 2 illustrates a conceptual diagram of a first medical image 200 of a breast according to a first imaging modality (e.g., x-ray mammogram). FIG. 3 illustrates a conceptual diagram of a second medical image 300 of a breast according to a second imaging modality (e.g., ultrasound). FIG. 4 illustrates a conceptual diagram of a bimodal medical image 400 formed by a superposition of the medical images 200 and 300. As indicated in FIG. 4, some of the features that are salient in one medical image (e.g., suspect regions 202 and 302) do not become enhanced or clarified by corresponding locations in the other image, and this information may be useful in determining a false positive or in further characterization of a suspect region. Conversely, some features that may not be particularly evident in either medical image may become apparent when the images are superimposed, as represented by the suspect region 402. Once again, it is to be appreciated that the example of FIGS. 2-4 is hypothetical in nature for communicating one or more principles according to the preferred embodiments, and is not a literal portrayal of breast images. However, analogous advantages apparent to the trained eye can be enjoyed by overlay of ultrasound thick-slice images and x-ray mammogram images of a breast, or vice versa, in accordance with the preferred embodiments.

Thus, in one preferred embodiment, one or more ultrasound thick-slice images are superimposed onto a corresponding x-ray mammogram view, the thick-slice images representing a slab-like volume of the breast taken parallel to a standard x-ray mammogram view. In other preferred embodiment, one or more ultrasound thick-slice images are superimposed onto a corresponding x-ray mammogram view, the thick-slice images representing a slab-like portion of the breast that is substantially less thick than the entire breast volume. This provides the advantage, not offered by the summation ultrasound image of U.S. Pat. No. 5,938,613, supra.

In yet another preferred embodiment, one or more ultrasound images of the breast are superimposed onto a corresponding x-ray mammogram view in a manner that allows for manual vernier adjustments of the registration of the images. It has been found that the manual vernier registration adjustments of the ultrasound images with the corresponding x-ray mammogram image is of substantial benefit in image analysis. In particular, it rapidly increases the viewer's perception and appreciation of breast structures being displayed by both component images, as compared to when (i) the component images are presented side-by-side, and (ii) the component images are displayed in fixed registration. Although precise explanations might well be left to cognitive scientists, it is believed that the generally amorphous nature of the breast images makes it difficult, when placed side-by-side, to mentally carry across distance and proportion information from one image to the other. This problem is alleviated somewhat when the images are superimposed and displayed in fixed registration with each other. However, especially with the medical image modalities at hand, it is still often difficult to perceive which component image is displaying which localized patterns in the fixed-registration bimodal image. When manual, vernier registration adjustments are performed according to the preferred embodiments, the subtle shifts of entire localized patterns responsive to the user's own adjustments can substantially enhance comprehension of the different localized patterns in both component images and in the overall bimodal image.

Figure 5:
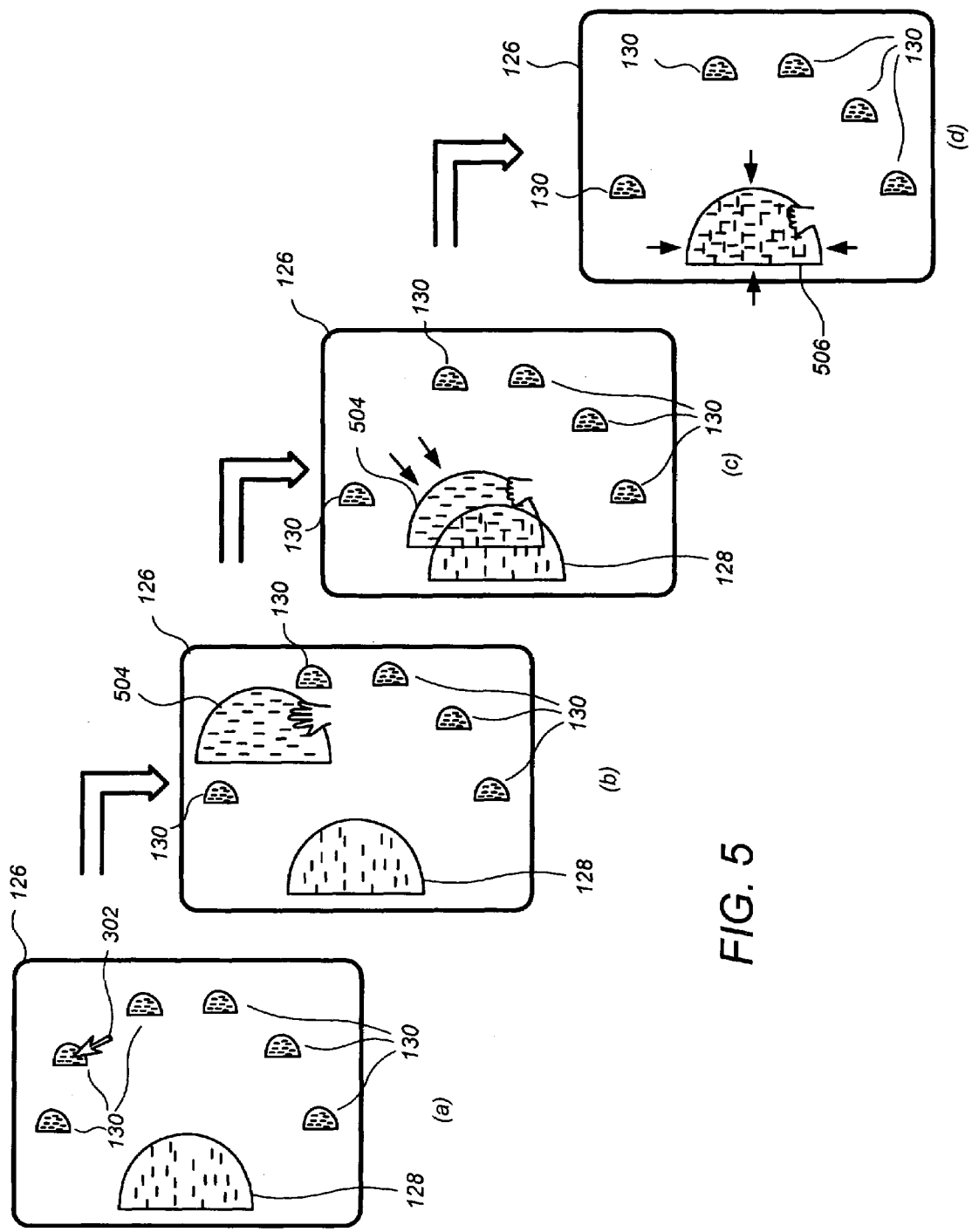
FIG. 5 illustrates an adjunct ultrasound display at different intervals during an overlay of an ultrasound image onto an x-ray mammogram image.

FIG. 5 illustrates the adjunct ultrasound display monitor 126 at different intervals during an overlay of an ultrasound image onto an x-ray mammogram image 128. In frame (a), the user first moves a cursor 502 over a particular ultrasound thick-slice thumbnail of interest. In frame (b), upon clicking the thick-slice thumbnail, the thumbnail is expanded to a full ultrasound thick-slice image 504 having the same spatial scale as the x-ray mammogram image 128. At frame (c), the user clicks-and-drags the ultrasound thick-slice image 504 over toward the x-ray mammogram image 128. At frame (d), a bimodal image 506 is displayed, with the user performing small, manual adjustments to the registration of the two component images forming the bimodal image. As the component images begin to overlap in frame (c), a mixing algorithm described further infra is used that approximates the visual effect of placing a conventional x-ray mammogram film on a light box, and superimposing a second transparency thereon containing a printed version of the thick-slice ultrasound image, although in general any of a variety of different mixing algorithms can be used to superimpose the component images.

Figure 6:
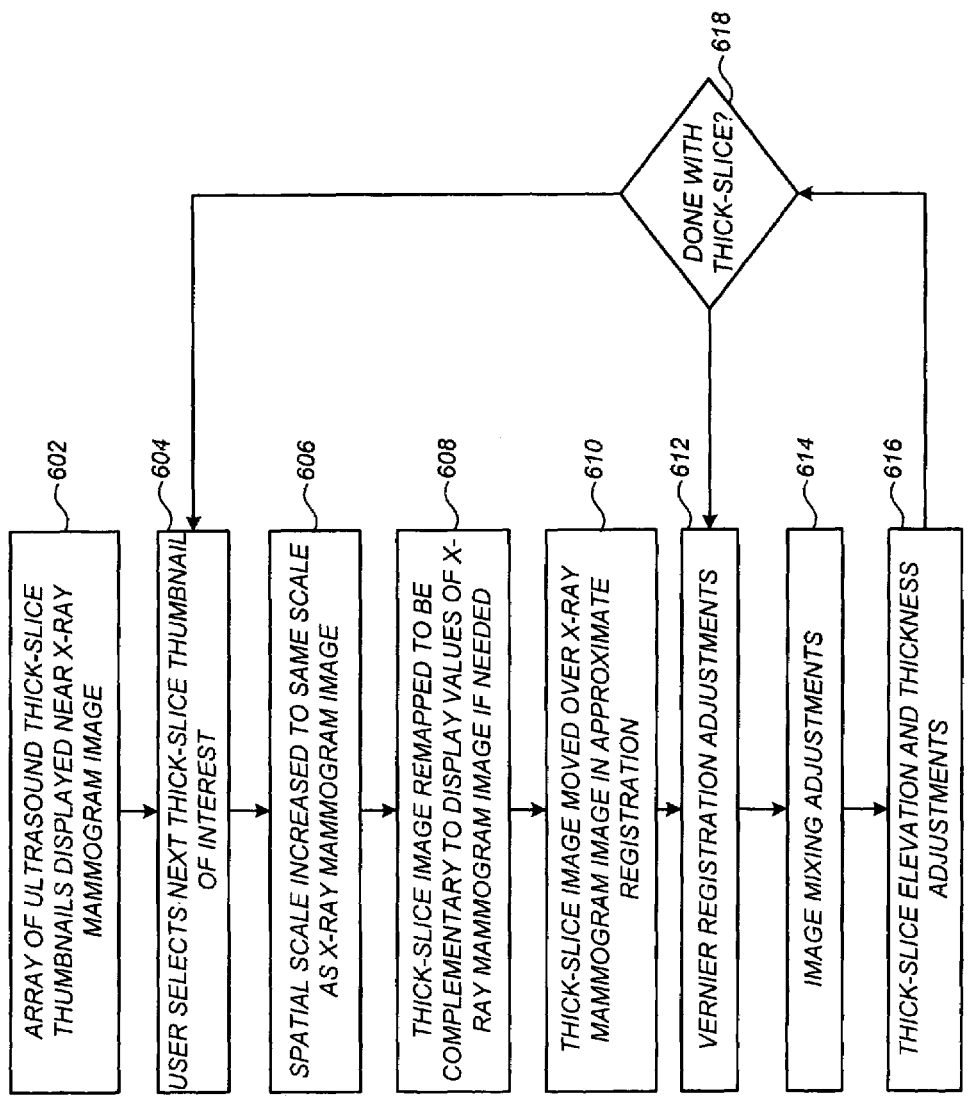
FIG. 6 illustrates steps corresponding to a method for breast cancer screening using an x-ray mammogram with adjunct ultrasound overlays according to a preferred embodiment.

FIG. 6 illustrates steps for breast cancer screening using an x-ray mammogram with adjunct ultrasound overlays according to a preferred embodiment. The steps of FIG. 6 are described with respect to a single x-ray mammogram view/breast pair (e.g., CC view for left breast), it being understood that analogous steps for the other breast/view pairs are being carried out serially or in parallel with the steps of FIG. 6. At step 602, an array of ultrasound thick-slice thumbnails is displayed near an x-ray mammogram image. At step 604, the user selects an ultrasound thick-slice thumbnail of interest. At step 606, the spatial scale of the ultrasound thick-slice thumbnail is increased to the same scale as the x-ray mammogram image. At step 608, the thick-slice ultrasound image is remapped, if necessary, to be complementary to the display values of the x-ray mammogram image.

At step 610, the thick-slice image is moved over the x-ray mammogram image in approximate or "starter" registration therewith. While in the embodiments of FIG. 5 this is described in terms of a manual click-and-drag process, the scope of the preferred embodiments is not so limited. In an alternative preferred embodiment, this step is performed automatically by the adjunctive ultrasound display system using methods known in the art, thereby saving radiologist time. Automated registration methods include those based on skin lines, nipple position, chest wall position, artificial external markers, natural internal feature markers such as visible microcalcifications, and/or other methods. Methods based on artificial external markers include those using a single "BB" or similar marker placed near the nipple, as well as those using three or more BBs. Where multiple artificial markers are used, the scaling of the component images may be contracted or expanded in one or both directions as necessary to get all of the markers to line up.

At step 612 the user performs manual vernier registration adjustments. When the previous initial registration step 610 is performed automatically rather than by manual manipulation, the vernier adjustments may be based on perceived registration differences in the initial registration. On the other hand, even if the initial registration is very good or perfect, the user still manipulates the component images to be slightly out-of-registration, and then moves them back into registration, in order to experience the benefits of the vernier image manipulations described supra. At step 614 the user may optionally perform mixing parameter adjustments as described infra with respect to FIGS. 13-14. At step 616 the user may optionally perform thick-slice elevation and thickness adjustments according to a "rolling thick-slice" method described infra with respect to FIG. 7. At step 618 the user may choose to continue the adjustment and analysis process or may proceed to another image view or thick-slice image.

Figure 7:
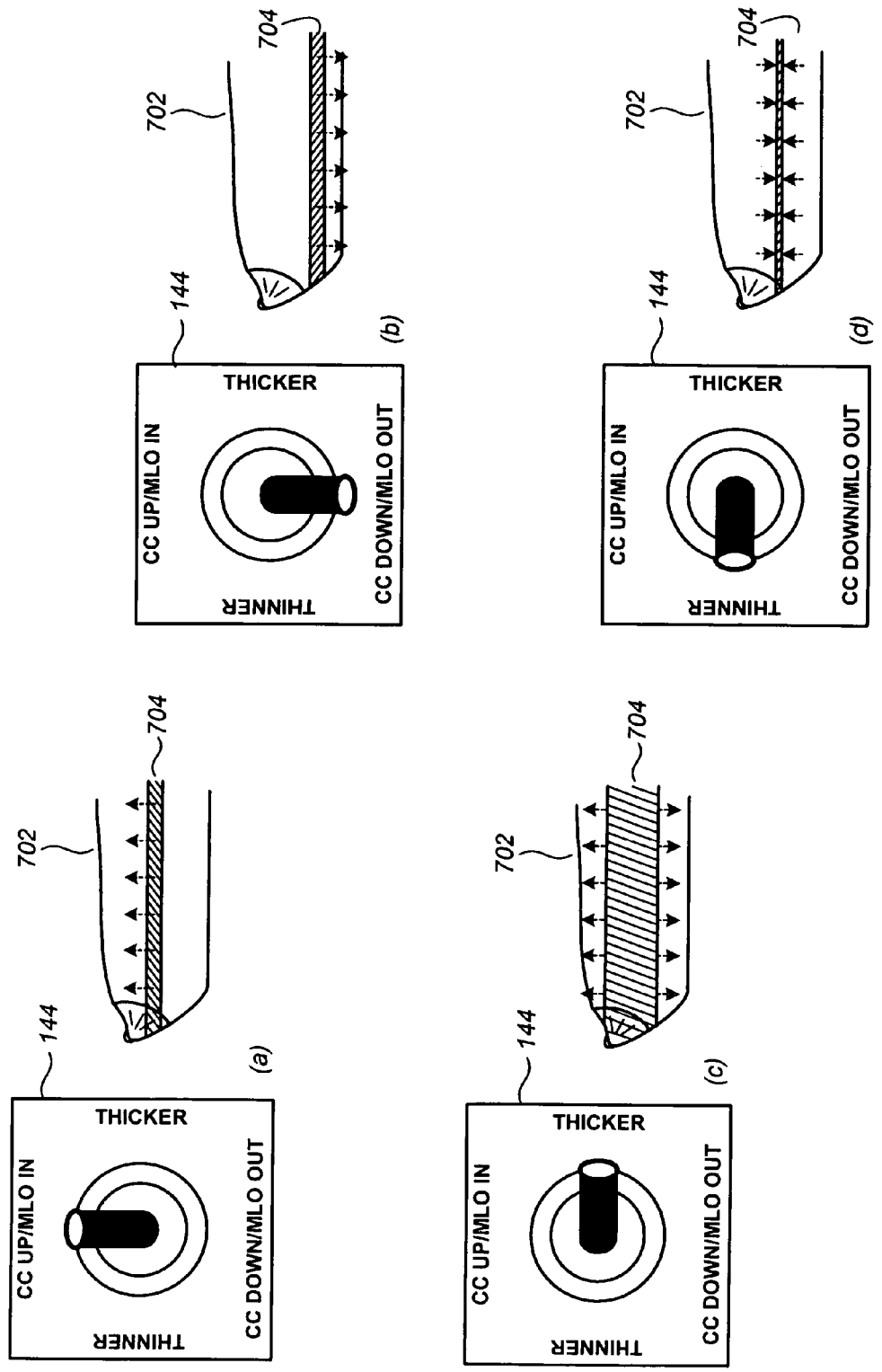
FIG. 7 illustrates a conceptual diagram of varying thick-slice elevation and thick-slice thickness using a dynamic control mechanism according to a preferred embodiment.

FIG. 7 illustrates a top view of the joystick control 144 of the adjunctive ultrasound screening station 108 of FIG. 1, along with a conceptual side view of a breast 702 and a slab-like thick-slice region 704 therein, for further describing the "rolling thick-slice" method of step 616 of FIG. 6, supra. For the CC view, when the joystick 144 is moved forward (frame (a)) or backward (frame (b)), the elevation of the thick-slice region 704 relative to a bottom compression plate is adjusted upward or downward, respectively, within the breast volume. For the MLO view, this elevation metric corresponds to a distance from the vertically-oriented compression plane for that view. More generally, if a non-standard plane is used, the elevation corresponds to a distance from one of the compression plates used to compress the breast. When the joystick 144 is moved right (frame (c)) or left (frame (d)), the thickness of the slab-like region whose data is used to form the thick-slice image is increased or decreased, respectively. Accordingly, the user may easily navigate throughout the breast volume, and may easily select between thinner and thicker-slice regions to compare to the x-ray mammogram. The thick-slice ultrasound image gently morphs along a continuum of two-dimensional representations in an intuitive manner that allows the radiologist to readily navigate the breast in both a positional sense (elevation) and abstractional sense (slab thickness).

FIGS. 8-14 illustrate a user display 800 according to a preferred embodiment at different points in a medical image superposition process according to a preferred embodiment. The user display 800 comprises a set of selection buttons 802, a patient identification display 822, and one or more medical images as described herein. Generally speaking, in addition to the capabilities described herein, all of the capabilities of the user display of Ser. No. 10/160,836, supra, are incorporated into the user display 800, such as the ability to display multiple thumbnail thick-slice images, select and expand a given thumbnail into a full-scale image, analyze individual slices and cine-presentations thereof throughout the breast volume, etc., as facilitated by the selection buttons 804-820. In the preferred embodiment of FIGS. 8-14, it is an x-ray mammogram image that is manually superimposed over a static thick-slice ultrasound image.

Figure 8:
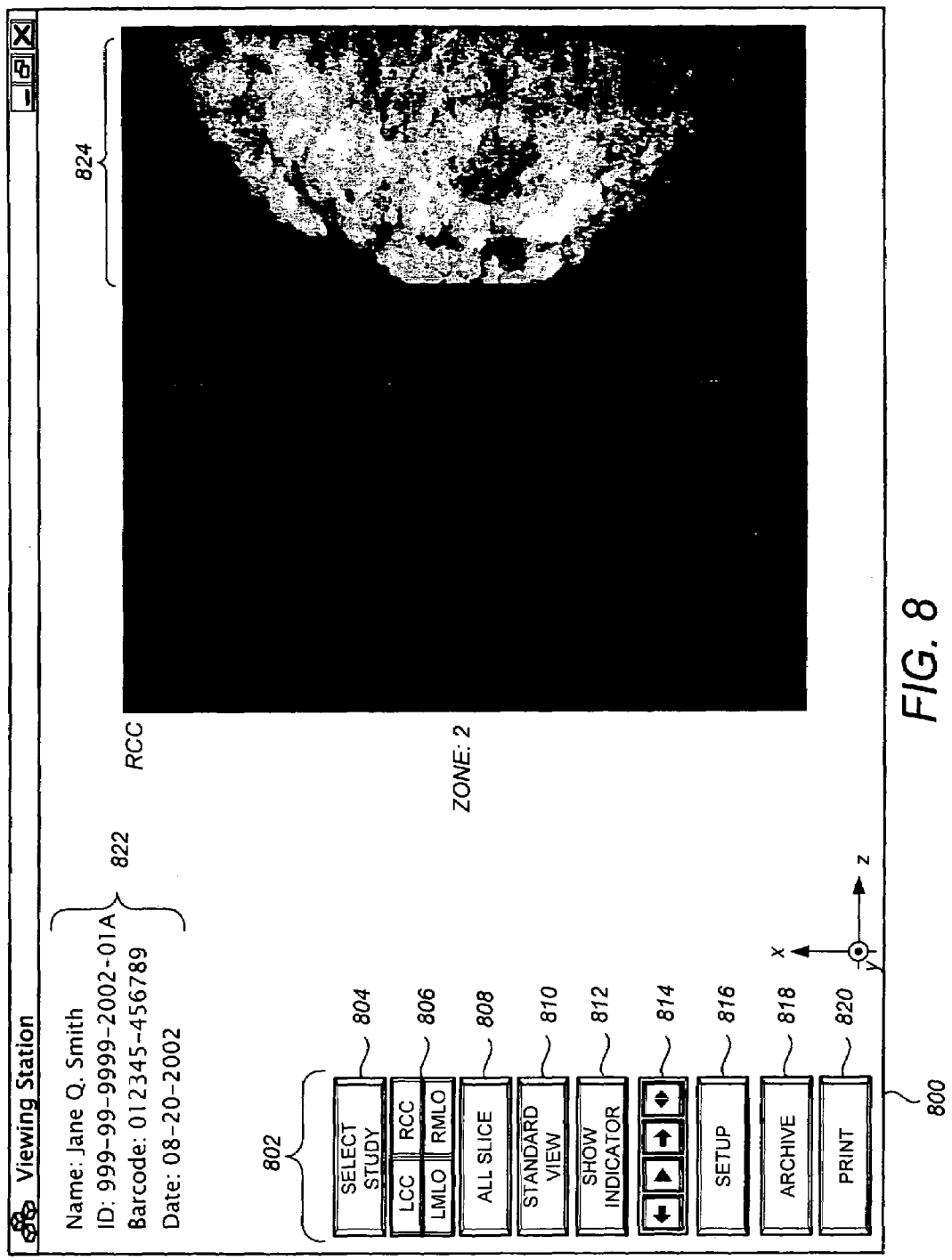
FIG. 8 illustrates an adjunct ultrasound display according to a preferred embodiment displaying an ultrasound thick-slice image.

FIG. 8 illustrates the user display 800 after a particular thick-slice image from a particular zone for the RCC view has been selected and expanded into the ultrasound image 824. The ultrasound image 824 is an 8-bit grayscale image with the gray scale selected to be reminiscent of a film-based x-ray mammogram as displayed on a light box, i.e., brightest=255=$D_{max}$=high acoustic echo and darkest=0=low acoustic echo.

Figure 9:
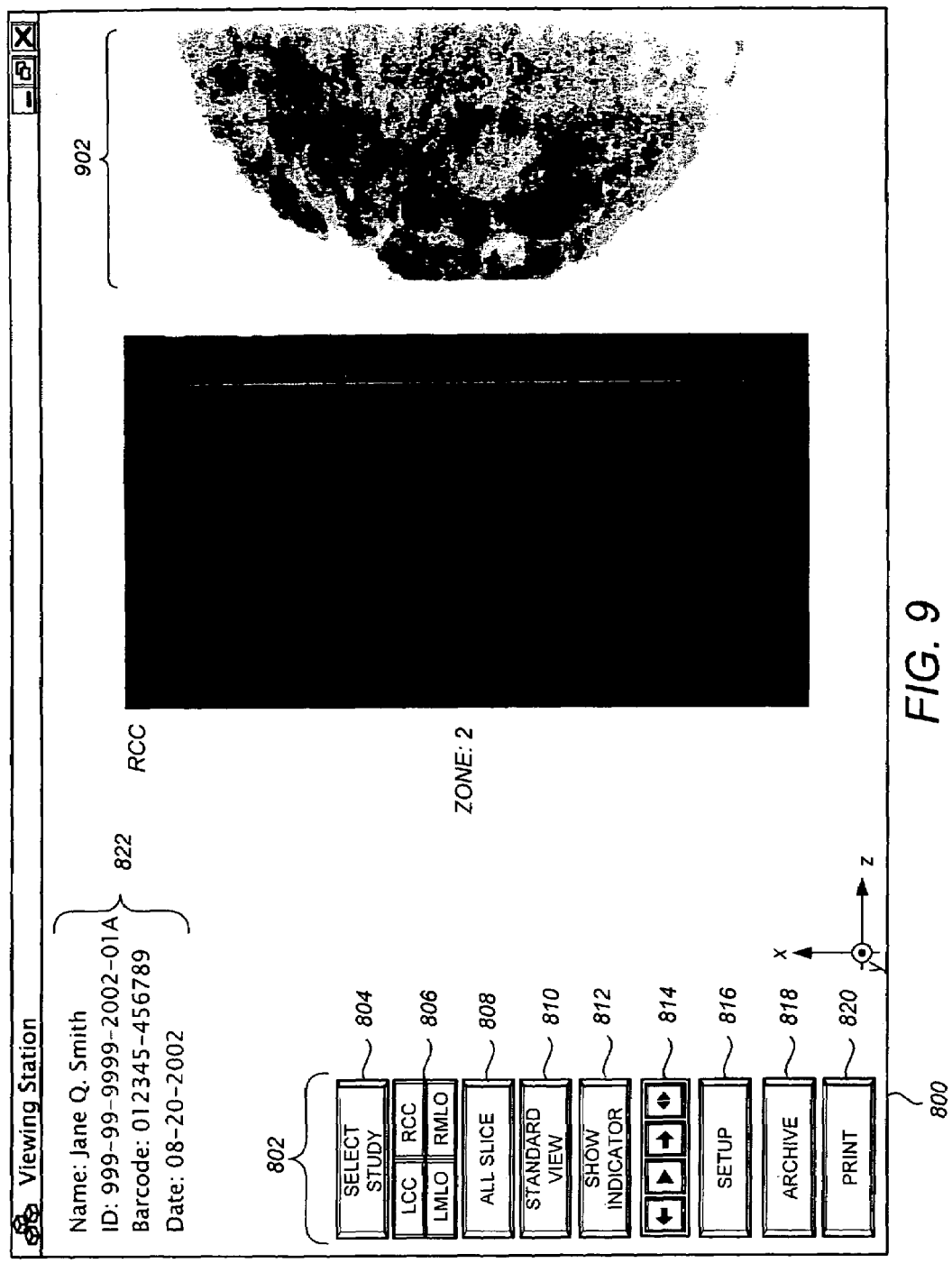
FIG. 9 illustrates an adjunct ultrasound display according to a preferred embodiment displaying a remapped version of the ultrasound thick-slice image of FIG. 8.

FIG. 9 illustrates the user display 800 upon user pressing of a first superposition key, such as the keyboard letter "I." Responsive to this command, the ultrasound image 824 is inverted such that brightest=255=$D_{max}$=low acoustic echo and darkest=0=high acoustic echo.

Figure 10:
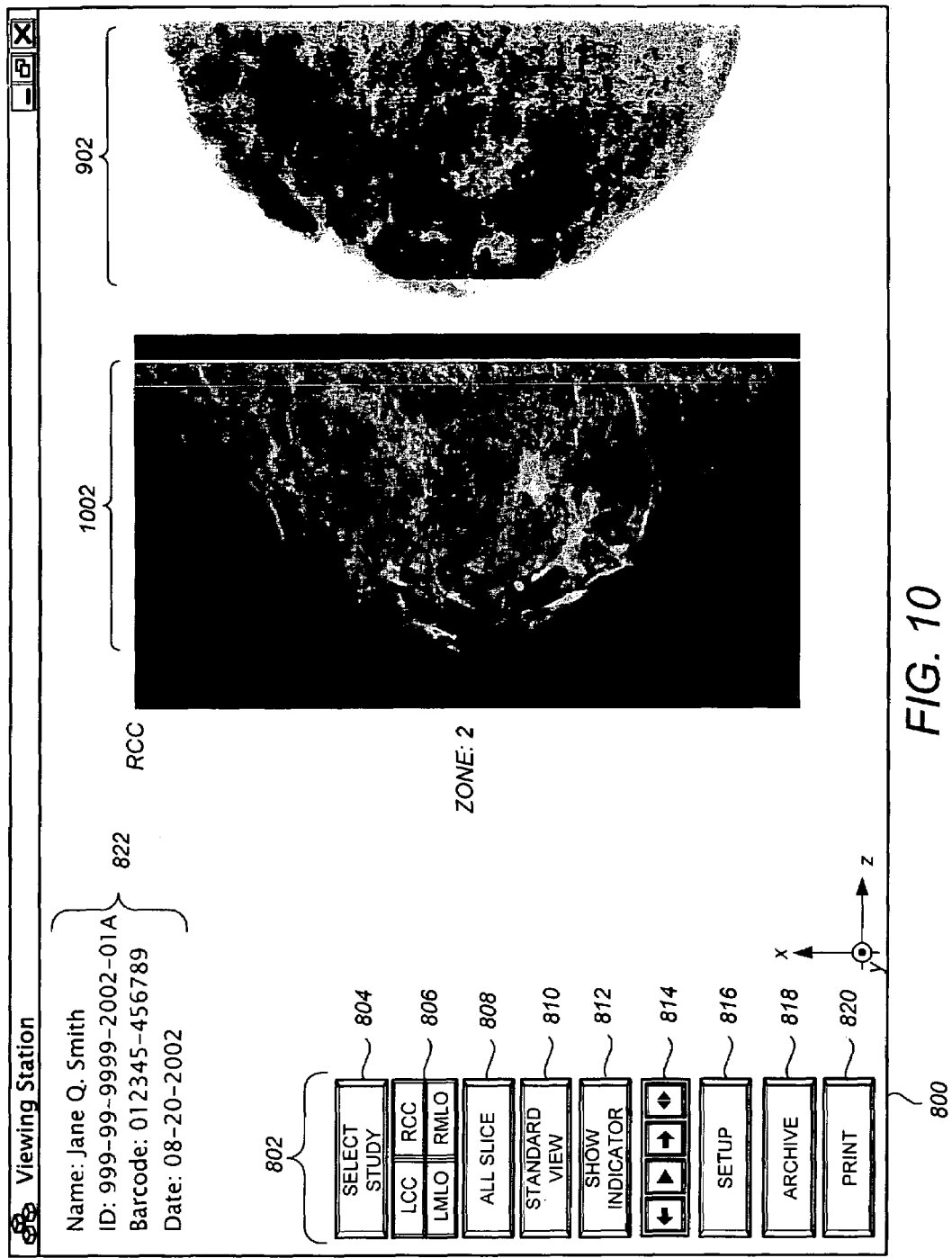
FIG. 10 illustrates an adjunct ultrasound display according to a preferred embodiment displaying a digital x-ray mammogram adjacent to the ultrasound thick-slice image of FIG. 9.

FIG. 10 illustrates the user display 800 upon user pressing of a second superposition key, such as the keyboard letter "M." Responsive to this command, an x-ray mammogram image 1002 is displayed near the ultrasound image 902. The x-ray mammogram image 1002 is an 8-bit grayscale image with the gray scale set to mimic the appearance of a film-based x-ray mammogram as placed on a light box, i.e., brightest=255=$D_{max}$=highly radio-opaque and darkest=0=highly radio-transparent.

Figure 11:
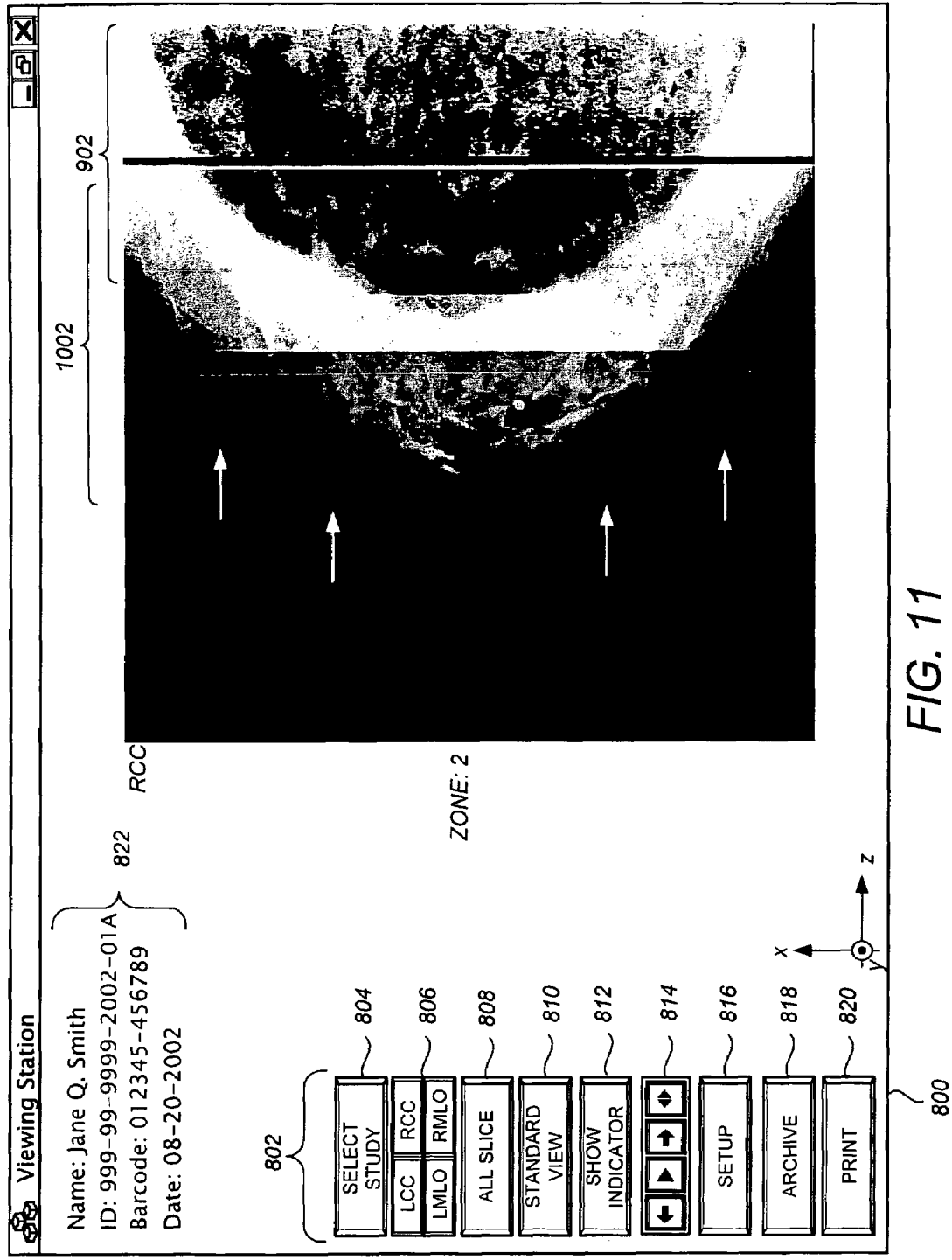
FIG. 11 illustrates an adjunct ultrasound display according to a preferred embodiment displaying the digital x-ray mammogram of FIGS. 9-10 as it is moved toward the ultrasound thick-slice image of FIGS. 9-10 for mixing therewith.

FIG. 11 illustrates the user display 800 as the user manually moves the x-ray mammogram image 1002 over the ultrasound image 902. In one preferred embodiment, the user manually causes lateral movement by pressing of the LEFT and RIGHT arrow keys of the keyboard and vertical movement by pressing the UP and DOWN arrows of the keyboard. At areas of image overlap, a pixelwise mixing algorithm is used to achieve superposition of the medical images. In one preferred embodiment illustrated in FIGS. 11-14, the mixing algorithm is given by Eq. (1) below, where (x,y) represents the coordinates of the pixel in question, u(x,y) is the value of the inverted ultrasound image 902 at that location, m(x,y) is the value of the x-ray mammogram image 1002 at that location, d(x,y) is the ultimate output display value at that location, and $F_{mix}$ is a scalar mixing factor valued between zero and unity:

$$d(x,y)=F_{mix} \cdot m(x,y)+(1-F_{mix}) \cdot u(x,y) \quad \{1\}$$

Preferably, the mixing factor $F_{mix}$ is dynamically user-adjustable, but will be assigned a default starting value of about 0.5. Any of a variety of mixing algorithms may be used in accordance with the preferred embodiments, and may be varied according to the specific display hardware used and the quality and dynamic range of the medical images used. In another preferred embodiment, the mixing algorithm is designed to closely emulate a film-based superposition scenario comprising (i) a light box, (ii) a standard film-based x-ray mammogram placed thereon (dark=radio-transparent, clear=radio-opaque), and (iii) an ultrasound image printed on a clear film placed thereon, the ultrasound image being printed such that dark=high acoustic echo and clear=low acoustic echo. This algorithm is given by Eq. (2) below, where $D_{max}$ is the brightest value available on the display monitor:

$$d(x,y)=D_{max}*[m(x,y)/D_{max}]*[u(x,y)/D_{max}] \quad \{2\}$$

Figure 12:
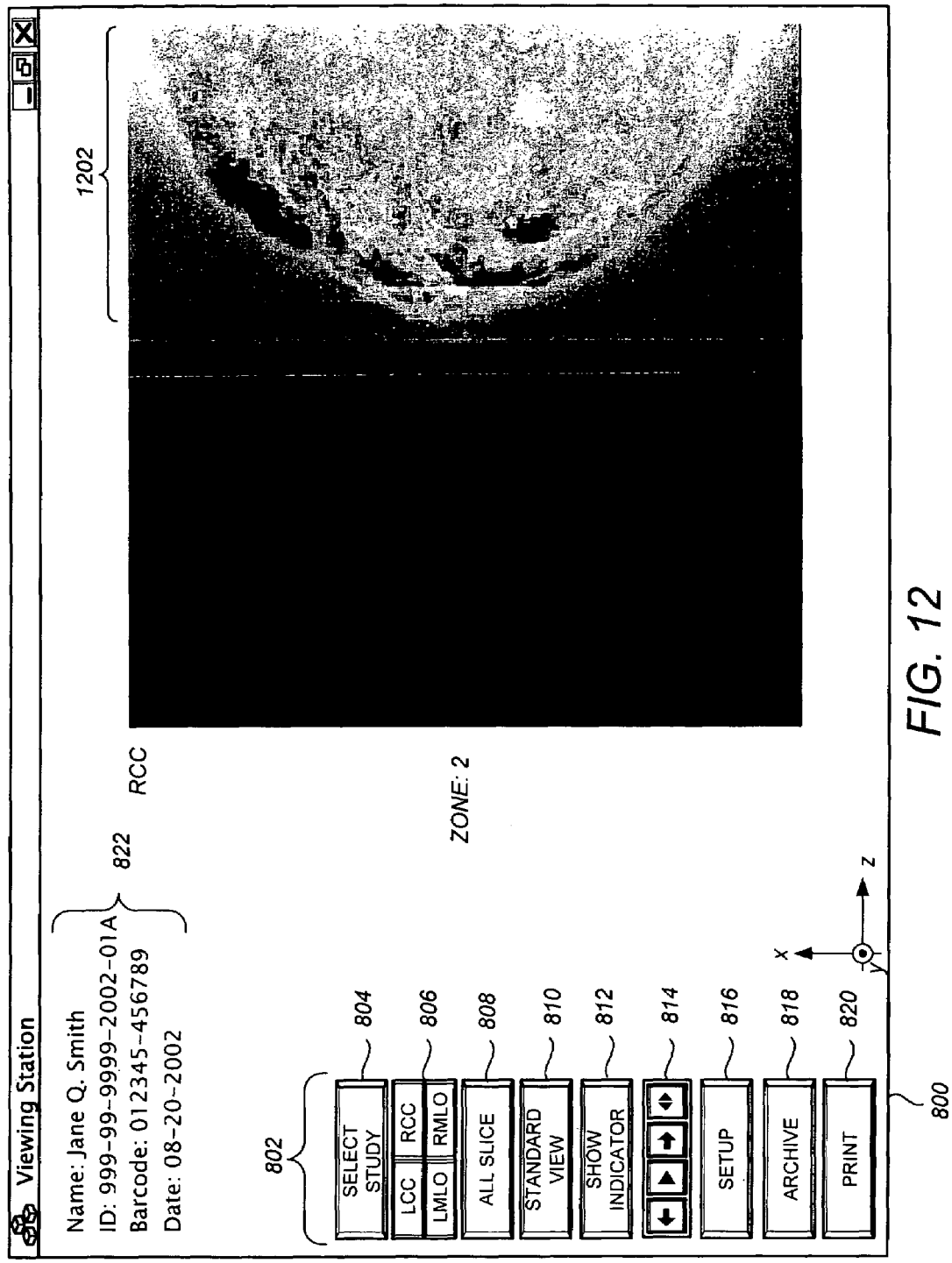
FIG. 12 illustrates an adjunct ultrasound display according to a preferred embodiment displaying a bimodal image of a digital x-ray mammogram superimposed upon an ultrasound thick-slice image and in approximate registration therewith.

FIG. 12 illustrates the user display 800 as registration of the component images is substantially achieved to form a bimodal image 1202. While viewing the bimodal image 1202, the user will usually be performing small manual adjustments of the registration of the component images by using the arrow keys, as described supra. During this process, the user may adjust the elevation and/or thickness of the thick-slice ultrasound image component in a "rolling thick slice" method described supra with respect to FIG. 7. Additionally, the mixing factor $F_{mix}$ may be dynamically adjusted, for example by using the "+" and "−" keyboard keys, so as to let one or the other of the component medical images predominate.

Figure 13:
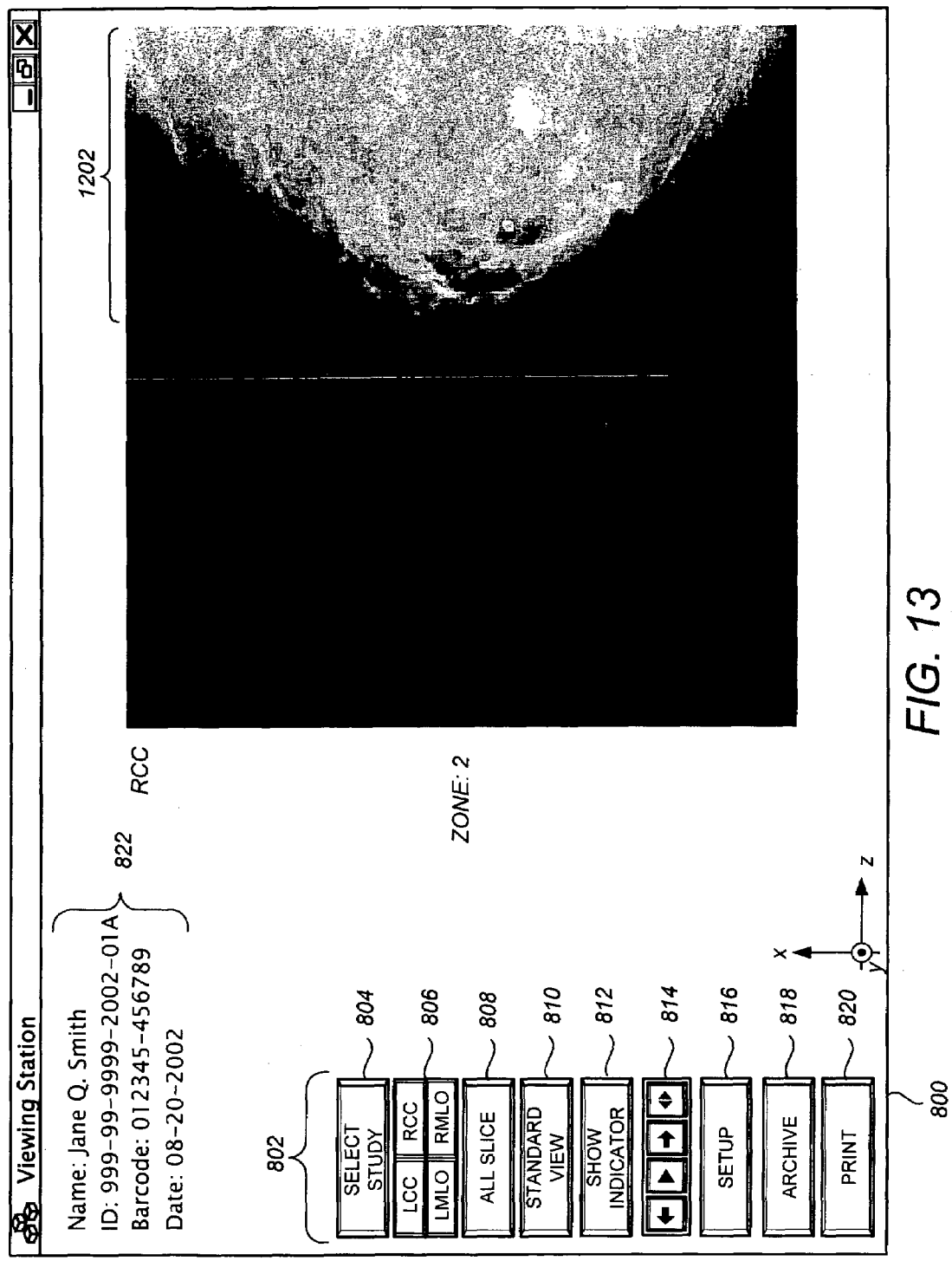
FIG. 13 illustrates an adjunct ultrasound display according to a preferred embodiment displaying the bimodal image of FIG. 12 as adjusted to allow its digital x-ray mammogram component to predominate over the ultrasound thick-slice image component.
Figure 14:
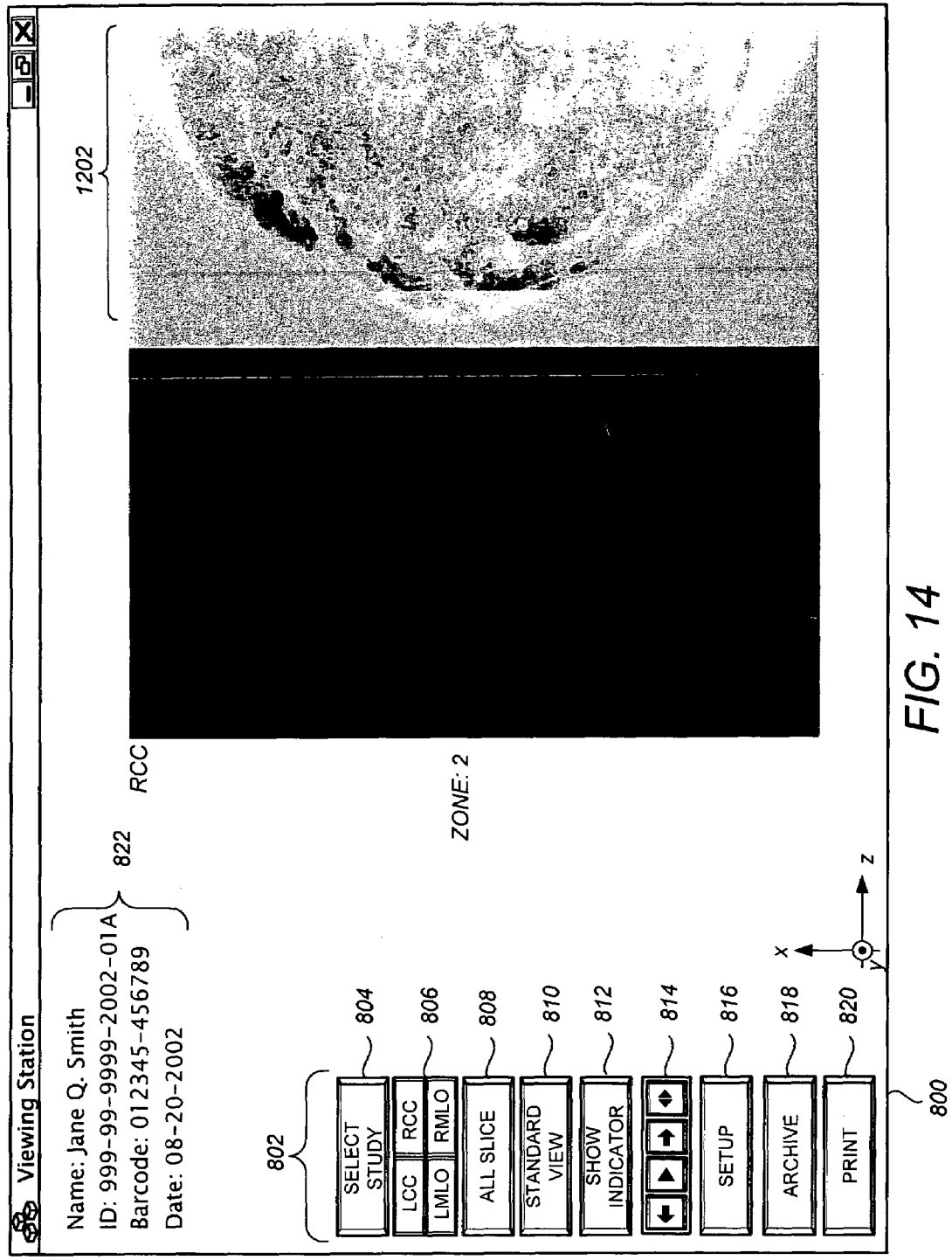
FIG. 14 illustrates an adjunct ultrasound display according to a preferred embodiment displaying the bimodal image of FIG. 12 as adjusted to allow its ultrasound thick-slice image component to predominate over its digital x-ray mammogram component.

FIG. 13 illustrates the user display 800 as the mixing factor $F_{mix}$ is adjusted closer to zero to let the x-ray mammogram image component predominate. FIG. 14 illustrates the user display 800 as the mixing factor $F_{mix}$ is adjusted closer to unity to let the ultrasound image component predominate.

It is to be appreciated that those preferred embodiments described supra in which both component images are displayed in electronic format are presented by way of non-limiting example only, and any of a variety of other component medical image display and bimodal image formation methods is within the scope of the preferred embodiments. For example, in another preferred embodiment, the x-ray mammogram is provided on a conventional x-ray film and placed on a lightbox, the lightbox being capable of back-projecting an ultrasound image onto its display surface. After reviewing the x-ray film in a conventional fashion, the radiologist may then activate this backprojection feature and thereby view an overlay of the x-ray mammogram image on the ultrasound image. In another preferred embodiment, a high-brightness computer display is used to illuminate an x-ray film for conventional viewing in a first configuration, and to display an ultrasound image in a second configuration that projects through the x-ray film to achieve an overlay of the x-ray mammogram image on the ultrasound image. In still another preferred embodiment, the x-ray mammogram is displayed digitally on a monitor or backprojected onto a light box, while the ultrasound image is printed onto a translucent film and placed on the monitor or light box.

In still another preferred embodiment, a standard film-based x-ray mammogram is placed on a lightbox, and an ultrasound image printed on a clear film is placed thereon and manually manipulated by the user. In such preferred embodiment, several thick-slice ultrasound images are printed on separate transparent sheets, which can be interchanged by the user as needed to achieve elevation variations, and which can be doubled-up or tripled-up as needed to represent thicker thick-slice regions of the breast volume.

In each case, the overlying and underlying medical images should be complementary to each other, and should be amenable to manual vernier registration adjustment by the user. Any of a variety of manual vernier registration adjustment techniques may be employed between the overlaid image and the underlying image.

For those preferred embodiments in which a first medical image is provided in film or other hardcopy format while a second medical image is provided in electronic display format, a bar code reader is included in the viewing station hardware. The bar code reader reads a bar code that is placed on each hardcopy image, using that bar code information to locate and access the second medical image from the system database.

Any of a variety of manual vernier registration adjustment techniques may be employed between the overlaid image and the underlying image, including touch-screen control, mouse or joystick control, trackball control, mechanical control, other techniques, or a combination of these techniques. For example, where both the x-ray image and ultrasound image are electronically displayed on the same display monitor, a click-and-drag technique using a computer mouse or joystick may be used. If one or both of the component images is on film or other hardcopy format, the radiologist may slide the overlying image across the underlying image by hand. Alternatively or in conjunction therewith, where the underlying image is achieved by back-projection or computer display, the underlying image may be manually shifted using by computer mouse click-and-drag, joystick, or trackball control.

Whereas many alterations and modifications of the present invention will no doubt become apparent to a person of ordinary skill in the art after having read the foregoing description, it is to be understood that the particular embodiments shown and described by way of illustration are in no way intended to be considered limiting. By way of example, although described supra in terms of adjunctive ultrasound screening, in view of the present disclosure one skilled in the art would readily be able to apply the thick-slice display apparatus of the preferred embodiments in the context of computerized tomography (CT) and/or magnetic resonance imaging (MRI) environments. In each case, individual image slices generated from CT scans or MRI scans of the breast are compounded so as to form thick-slice images of slab-like portions of the breast along planes parallel to a standardized x-ray mammogram view plane, and the thick-slice images are displayed in close proximity to an x-ray mammogram of the breast in a way that allows them to be manually translated and superimposed thereon by the radiologist. The elevation and/or depth CT or MRI thick-slice images may be adjusted by manual joystick control or other control mechanism.

By way of further example, while described supra in terms of the superposition of only a single thick-slice ultrasound image over an x-ray mammogram (or vice versa), in other preferred embodiments two or more thick-slice ultrasound images are superimposed with the x-ray mammogram. Moreover, the two or more thick-slice images may correspond to non-adjacent portions of the breast volume. In still other preferred embodiments, it has been found that useful observations may be made by superimposing two ultrasound thick-slice images taken from the same region of the breast at different points in time, e.g., spaced 1 year apart, to assist in screening for changes in the breast over time. The two superimposed thick-slice images may be superimposed upon an x-ray mammogram image, or alternatively can be displayed without the x-ray mammogram image. In other preferred embodiments, three or more thick-slice ultrasound images are superimposed corresponding to three or more different points in time. In still other preferred embodiments, a plurality of x-ray mammogram images taken at different points in time can be superimposed with a plurality of thick-slice ultrasound images taken at different points in time. Methods for implementing systems according to these preferred embodiments would be readily apparent to those skilled in the art in view of the present disclosure.

By way of further example, while described supra in terms of the superposition of images from two different modalities, the features and advantages of the preferred embodiments are readily applied to the superposition of medical images from three different modalities, e.g., ultrasound, x-ray mammogram, and MRI. According to a preferred embodiment, for those modalities that yield three-dimensional information, thick-slice images are derived therefrom and used for overlay purposes. Exemplary combinations may include overlays of: (i) x-ray mammogram, ultrasound, and MRI; (ii) (ii) x-ray mammogram, ultrasound, and CT; (iii) CT, ultrasound, and MRI; (iv) CT, x-ray mammogram, and MRI; and others. The features and advantages of the preferred embodiments are also readily applied to the superposition of medical images from four or more different imaging modalities. For such multi-modality cases, in order to reduce the amount of clutter and to derive more utility from the overlays, the individual medical images are preferably enhanced prior to or during overlay so as to display the most salient features revealed by its respective imaging modality. By way of example, the ultrasound image will be spatially low-pass filtered to concentrate on larger features, it being understood that very small structures such as microcalcifications are not strongly revealed by the ultrasound modality. The reduced amount of speckle from the low-pass filtering will reduce the amount of clutter in the multi-modality overlay image.

Moreover, it is to be appreciated that the features and advantages of the preferred embodiments are applicable to medical imaging formats not currently contemplated for use in large-scale breast cancer screening programs. For example, phase information from holographically encoded medical images may be interferometrically combined to achieve the medical image superpositions, or other types of time- or space-based modulation methods may be used to encode and superimpose the medical images. Therefore, reference to the details of the preferred embodiments are not intended to limit their scope, which is limited only by the scope of the claims set forth below.

What is claimed is:

1. A method for facilitating review of information representative of a three-dimensional breast ultrasound volume, comprising:
  displaying a two-dimensional thick-slice ultrasound image representative of a sonographic property of the breast within a slab-like subvolume thereof, said slab-like subvolume having a thickness in a range of 2 mm to 20 mm and an elevation from a reference plane;
  receiving a user request to vary at least one of the elevation and the thickness of the slab-like subvolume; and
  modifying in real time the displayed two-dimensional thick-slice image according to variations made to the at least one of the elevation and thickness of said slab-like subvolume responsive to said user request.

2. The method of claim 1, wherein said variations made to the at least one of the elevation and thickness are smoothly continuous such that the modifications to the two-dimensional thick-slice image appear morphable rather than instantaneous.

3. The method of claim 2, wherein said user requests are received from an input device having, for each of said elevation and said thickness, an "off" position indicative of no request for variation and at least one "on" position indicative of a request for variation, whereby a look and feel of physical navigation through an elevation-thickness space is achieved.

4. The method of claim 1, wherein said reference plane corresponds to a plane of a compression plate against which the breast was compressed during a volumetric ultrasound scan thereof that yielded the three-dimensional breast ultrasound volume.

5. The method of claim 4, said reference plane comprising a standard x-ray mammogram view plane, further comprising displaying an x-ray mammogram image of the breast taken along said standard x-ray mammogram view plane, said x-ray mammogram image being displayed in close proximity to said thick-slice image for substantially simultaneous viewing therewith.

6. The method of claim 5, wherein said x-ray mammogram image is displayed as an overlay with said thick-slice image and in substantial registration therewith.

7. The method of claim 6, wherein said x-ray mammogram image comprises one of (i) a film-based image physically overlaid on a display monitor displaying said thick-slice image, and (ii) a softcopy image digitally mixed with said thick-slice image.

8. An apparatus for facilitating review of information representative of a three-dimensional breast ultrasound volume, comprising:
  a display device; and
  a processor coupled with the display device and generating for viewing thereon a two-dimensional thick-slice ultrasound image representative of a sonographic property of the breast within a slab-like subvolume thereof, said slab-like subvolume having a thickness in a range of 2 mm to 20 mm and an elevation from a reference plane;
  a user input device for receiving a user request to vary at least one of the elevation and thickness of the slab-like subvolume, said processor varying the at least one of the elevation and thickness responsive to said user request, said processor modifying in real time the two-dimensional thick-slice image according to said variations of the at least one of the elevation and thickness for real time viewing on said display device.

9. The apparatus of claim 8, said processor varying the at least one of the elevation and thickness in a smoothly continuous manner such that the modifications to the two-dimensional thick-slice image appear morphable on said display device rather than instantaneous.

10. The apparatus of claim 9, said user input device comprising, for each of said elevation and said thickness, an "off" position indicative of no request for variation and at least one "on" position indicative of a request for variation, whereby a look and feel of physical navigation through an elevation-thickness space is provided to the user.

11. The apparatus of claim 8, wherein said reference plane corresponds to a plane of a compression plate against which the breast was compressed during a volumetric ultrasound scan thereof that yielded the three-dimensional breast ultrasound volume.

12. The apparatus of claim 11, said reference plane comprising a standard x-ray mammogram view plane, said processor further generating for viewing on the display device in close proximity to said thick-slice image an x-ray mammogram image of the breast taken along said standard x-ray mammogram view plane.

13. The apparatus of claim 12, wherein said x-ray mammogram image is displayed as an overlay with said thick-slice image and in substantial registration therewith.

14. The apparatus of claim 13, wherein said x-ray mammogram image comprises a softcopy image digitally mixed with said thick-slice image.

15. A computer program product stored on a computer-readable medium for facilitating review of information representative of a three-dimensional breast ultrasound volume, comprising:
  computer code for displaying a two-dimensional thick-slice ultrasound image representative of a sonographic property of the breast within a slab-like subvolume thereof, said slab-like subvolume having a thickness in a range of 2 mm to 20 mm and an elevation from a reference plane;
  computer code for receiving a user request to vary at least one of the elevation and the thickness of the slab-like subvolume; and
  computer code for modifying in real time the displayed two-dimensional thick-slice image according to variations made to the at least one of the elevation and thickness of said slab-like subvolume responsive to said user request.

16. The computer program product of claim 15, wherein said variations made to the at least one of the elevation and thickness are smoothly continuous such that the modifications to the two-dimensional thick-slice image appear morphable rather than instantaneous.

17. The computer program product of claim 16, wherein said computer code for receiving is configured to receive user requests from an input device having, for each of said elevation and said thickness, an "off" position indicative of no request for variation and at least one "on" position indicative of a request for variation, whereby a look and feel of physical navigation through an elevation-thickness space is achieved.

18. The computer program product of claim 15, wherein said reference plane corresponds to a plane of a compression plate against which the breast was compressed during a volumetric ultrasound scan thereof that yielded the three-dimensional breast ultrasound volume.

19. The computer program product of claim 18, said reference plane comprising a standard x-ray mammogram view plane, further comprising computer code for displaying in close proximity to said thick-slice image an x-ray mammogram image of the breast taken along said standard x-ray mammogram view plane.

20. The computer program product of claim 19, wherein said x-ray mammogram image is displayed by said computer code for displaying as an overlay with said thick-slice image and in substantial registration therewith.

* * * * *